| United States Patent [19] | [11] 4,042,704 |
| --- | --- |
| Coombs | [45] Aug. 16, 1977 |

[54] BENZINDAZOLES

[75] Inventor: Robert V. Coombs, Chatham, N.J.

[73] Assignee: Sandoz, Inc., East Hanover, N.J.

[21] Appl. No.: 668,266

[22] Filed: Mar. 18, 1976

[51] Int. Cl.$^2$ .......................................... C07D 231/56
[52] U.S. Cl. ............................ 424/273 P; 260/296 T; 548/371
[58] Field of Search ..................... 260/310 C; 424/273

[56] References Cited
PUBLICATIONS

Duewell et al., Chem. Abst., vol. 68, 49502h, 1968.
Belykh et al., Chem. Abst., vol. 77, 19574b, 1972.

*Primary Examiner*—Lorraine A. Weinberger
*Assistant Examiner*—Jane T. Fan
*Attorney, Agent, or Firm*—Gerald D. Sharkin; Richard E. Vila; Frederick H. Weinfeldt

[57] ABSTRACT

The compounds are benz[f]indazoles, e.g., 3-(p-chlorophenyl)-1-methylbenz[f]indazole, and are useful as fertility control agents.

41 Claims, No Drawings

BENZINDAZOLES

This invention relates to organic compounds and more particularly to benz [f]indazoles and their pharmaceutically acceptable acid addition salts, as well as to pharmaceutical compositions containing such compounds, and their use as pharmaceutical agents.

The compounds of the invention are conveniently represented by the formula I:

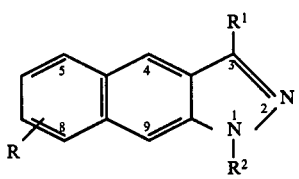

wherein
R is a hydrogen atom, halo having an atomic weight of from about 18 to 80, i.e., fluoro, chloro or bromo, or alkyl or alkoxy having from 1 to 4 carbon atoms;
$R^1$ is a member of the group consisting of:
  a. tertiary butyl;
  b. pyridyl (which may be bound at the 2, 3 or 4-position; and
  c. substituted or unsubstituted phenyl of the structure:

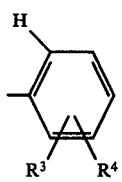

in which $R^3$ and $R^4$ are selected independently from the group consisting of a hydrogen atom, alkyl having from 1 to 4 carbon atoms, e.g., methyl, alkoxy having from 1 to 4 carbon atoms, e.g., methoxy, and halo having an atomic weight of from about 18 to 80, i.e., fluoro, chloro or bromo; and
$R^2$ is a hydrogen atom or alkyl having from 1 to 4 carbon atoms, e.g., methyl, or alkenyl or alkynyl having from 2 to 4 carbon atoms, e.g., allyl, or propargyl; provided that:
  1. when R is bromo then $R^1$ is other than types a) or b), i.e., it is of type c);
  2. when $R^3$ and $R^4$ are on adjacent carbons, they are not both branched alkyl or alkoxy; and
  3. when R is bromo and $R^3$ is chloro or bromo, then $R^4$ is not chloro or bromo.

The class of Compounds I, then consists of two subclasses of compounds depending upon the nature of $R^2$, i.e., Compounds Ia:

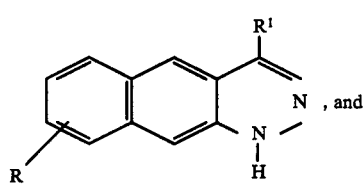

compounds Ib:

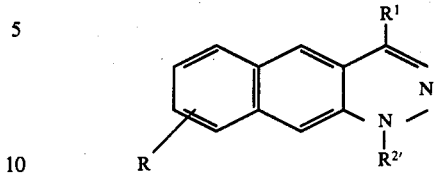

in which R and $R^1$ are as defined above, and $R^{2'}$ is the same as $R^2$ as defined above, when it is not a hydrogen atom, i.e., it is a hydrocarbyl (alkyl, alkenyl or alkynyl).

Compounds Ia are obtainable by reacting (process a) 3-carbonyl-2-naphthols of formula II:

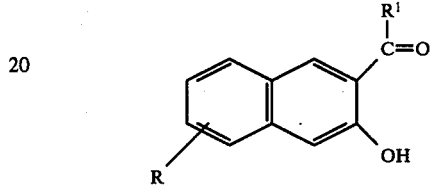

in which R and $R^1$ are as defined above with hydrazine (compound III). Process a) is carried out at moderate temperatures, e.g., from about 40° to 250° C. An inert organic solvent may be used, e.g., diethylene glycol (i.e., bis-(2-hydroxyethyl) ether), diglyme or triglyme, preferably, diethylene glycol. However, excess hydrazine may serve as all of or part of the solvent. It is particularly convenient to carry out the reaction at the reflux temperature of the reaction mixture. Hydrazine hydrate may be employed directly as the source of hydrazine.

If desired, Compounds Ib may be prepared directly from Compounds II by reaction (process a') of a hydrazine of formula III'

III'. $H_2N-NHR^{2'}$ in which $R^{2'}$ is as defined above, Process a') may be carried out under the general conditions as described above for process a).

A preferred method of obtaining Compounds Ib is to prepare them by process b) which involves introduction of a hydrocarbyl substituent, i.e., $-R^{2'}$ (as defined above), at the 1-position of a 1-alkali metal salt of a compound Ia':

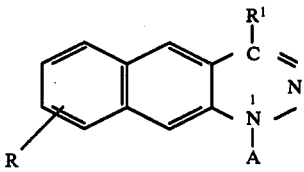

in which R and $R^1$ are as defined above, and A is a cation of an alkali metal, i.e., sodium, lithium or potassium, preferably sodium, by reacting a compound Ia' with a hydrocarbylating agent of the formula IV:

 $R^{2'}-X$ (IV)

in which $R^{2'}$ is as defined above and X is a leaving group, e.g., a halogen having an atomic weight of from about 34 to 127, i.e., chloro, bromo or iodo, or the residue of an organic sulfonate, e.g., tosylate, preferably iodo, in a suitable inert solvent, under anhydrous conditions. It is preferred to employ the hydrocarbylating agent (IV) in excess, e.g., from about 5 to 20 fold equivalents. While temperatures are not critical, it is convenient to carry out the reaction from about 35° to 100° C., particularly at from about 60° to 85° C. a suitable inert organic solvent is, for example, dimethylacetamide (DMA). Where the hydrocarbylating agent (IV) is a liquid, an excess thereof may serve as all or part of the solvent.

Compounds Ia' may be prepared in a conventional manner for preparation of an alkali metal salt of a secondary amine (a nitrogen atom having one available hydrogen atom), i.e., process b'). Process b') may be carried out, for example, by treating a Compound Ia in a suitable inert solvent, e.g., DMA, with an alkali metal-contributing agent, e.g., an alkali metal hydride or amide under anhydrous conditions at moderate temperatures, e.g., from about 15° to 50° C., preferably at room temperature. The resulting compounds Ia' may then be utilized for process b). A Compound Ia' need not be employed in isolated form; it being particularly convenient to carry out process b) by reacting a compound Ia' in situ, that is, in the reaction mixture obtained in preparation thereof. The solvent used in process b') thus may serve as the solvent for process b). As anhydrous conditions are employed in both processes b) and b'), it is preferable to carry them out under an inert atmosphere, e.g., under dry nitrogen. It is also preferred to utilize the alkali metal-contributing agent in finely divided form in an inert hydrocarbon, e.g., when A=Na, sodium hydride suspended in mineral oil.

The above-described methods for preparing compounds Ia and Ib may be represented by Reaction Scheme A-B, below, in which the above-mentioned compounds and reagents are shown; R, R¹, R²', A and X being as defined above:

REACTION SCHEME A-B

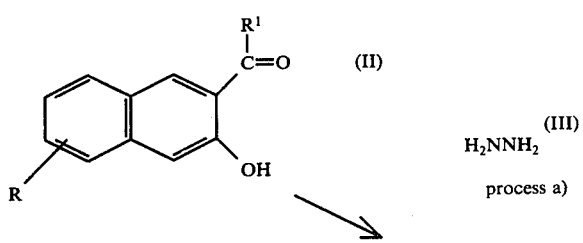

-continued
REACTION SCHEME A-B

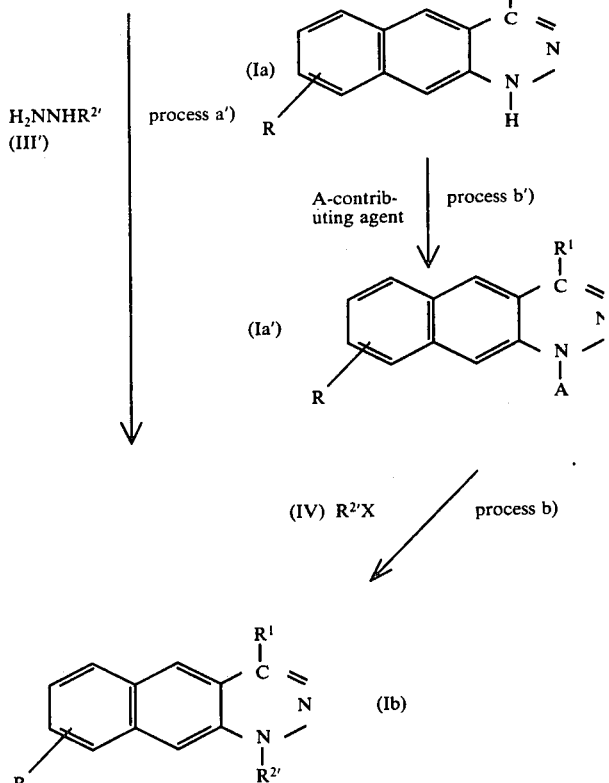

Compounds II, (the starting materials for processes a and a') are known and may be prepared as described in the literature, or where a particular form of Compound II is novel it may be prepared in a manner analogous to the descriptions in the literature for preparing those Compounds II which are known.

A convenient method for preparing certain compounds II, i.e., the subclass of compounds II':

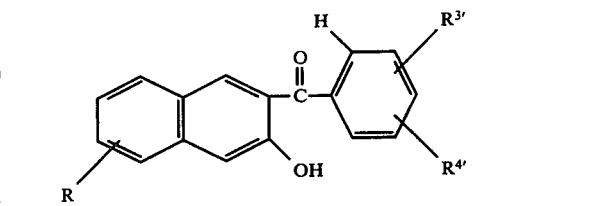

in which R is as defined above, and R³' and R⁴' are the same as R³ and R⁴, as defined above, except that:

1. when one of R³' or R⁴' is other than a hydrogen atom then one of R³' and R⁴' which is other than a hydrogen atom must be located at the 4-position, i.e., para; and 2. when R³' is chloro or bromo then R⁴' is neither chloro nor bromo, involves 2 steps (process c). The first step involves halogenating (Step 1) a 2-hydroxy-3-naphthoic acid of formula V:

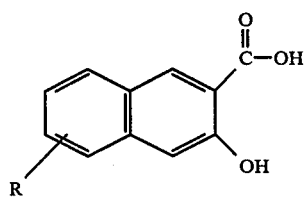

in which R is as defined above, to obtain a corresponding acyl halide, i.e., a compound VI:

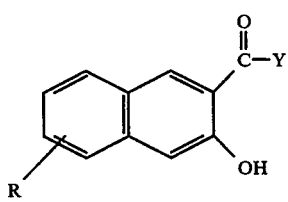

in which R is as defined above, and Y is a halogen having an atomic weight of from about 34 to 80, i.e., chloro or bromo, which acyl halide is then treated by a Friedel-Crafts reaction (Step 2) with a reagent of formula VII:

in which $R^{3'}$ and $R^{4'}$ are as defined above, to introduce the type c) substituent.

In the above-outlines Process c), Step 1, the halogenation, may be carried out in a conventional manner for converting a carboxylic acid to the corresponding acyl halide for treatment with a halogenating agent. The selection of the particular halogenating agent and conditions employed depends on what particular halide is desired as Y, i.e., chloro or bromo. Step 1), may be carried out with a suitable halogenating agent, e.g., thionyl chloride, thionyl bromide, phosphorus pentachloride or phosphorus pentabromide, in an organic solvent which is inert under the reaction conditions, e.g., chloroform or benzene, at a temperature from about 20° to the reflux temperature of the reaction mixture. An excess of the halogenating agent may, however, be used in place of the solvent if it is a liquid under the reaction conditions. The reaction product may be recovered by conventional means. Y is preferably chloro, and a preferred halogenating agent is thionyl chloride.

Suitable catalysts for Step 2, are the well-known Friedel-Crafts catalysts, e.g., aluminum or ferric trichloride or tribromide, particularly $AlCl_3$. Step 2 is carried out under the conditions conventionally applied in carrying out Friedel-Crafts reactions, e.g., anhydrous conditions are employed, and the reaction may be carried out in an inert organic solvent, e.g., carbon disulfide, nitrobenzene or an aliphatic hydrocarbon such as hexane, or cyclohexane. However, it is preferred that where the reagent (VII) is liquid under the reaction conditions, an excess thereof be employed as part or all of the solvent, as well as to insure the presence of an excess of reagent to enhance the reaction. The reaction may be run at, for example, at from about 45° to 200° C., preferably at the reflux temperature of the reaction mixture.

The above-described process c) for preparing Compounds II', may be conveniently represented by Reaction Scheme C, below, in which R, $R^{3'}$, $R^{4'}$ and Y are as defined above:

REACTION SCHEME C

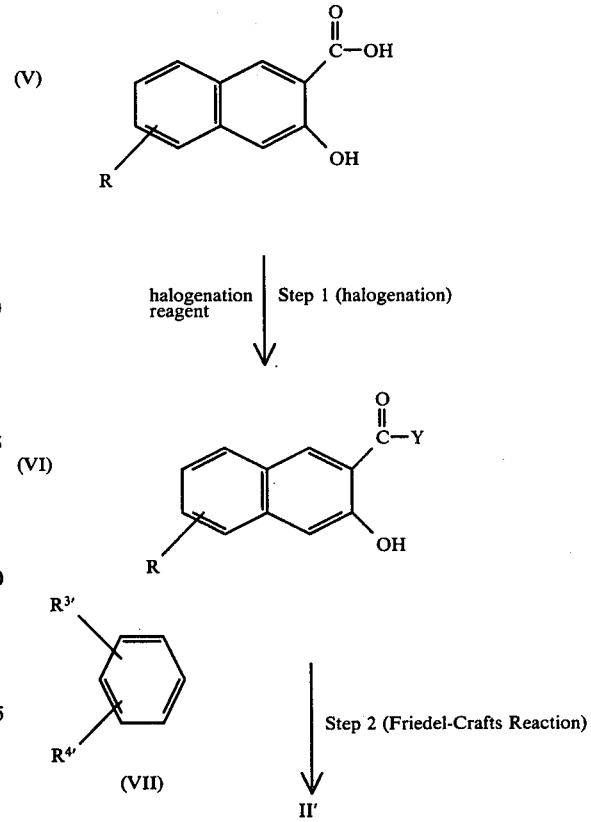

While the above-described process c) is convenient for preparing most of the compounds II in which $R^1$ is of type c), it is not entirely satisfactory for preparing those compounds II in which $R^3 = R^4 =$ Br or Cl; or $R^3 =$ Cl and $R^4 =$ Br, because the appropriate reagents analogous to compounds VII are relatively sluggish under Friedel-Crafts reaction conditions, e.g., dichlorobenzene. Hence, the c) radical cannot bear two substituents which are halogens having an atomic weight of from about 34 to 80. It will also be noted that unless the c) radical is other than unsubstituted phenyl, there must be at least one substituent at the para-position. However, the balance of compounds II, (except where R is bromo) i.e., compounds II":

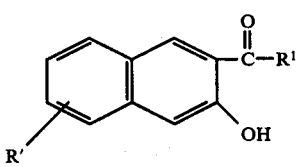

in which $R^1$ is as defined, and R' is the same as R as defined above except that it is not bromo, may be prepared by an "acylation reaction" (process d) which involves reacting a 3-lithiated tetrahydropyranyl ether of a 2-naphthol, i.e., a compound VIII:

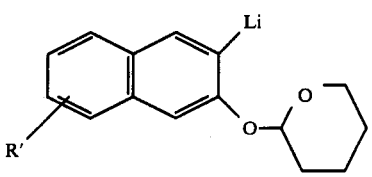
(VIII)

in which R' is as defined above, with a $R^1$-acyl group-introducing reagent of formula IX:

$$R^1-Q \qquad (IX)$$

in which $R^1$ is as defined above, and Q is either a carboxylate- or nitrile group.

Compounds VIII are obtainable by "lithiating" corresponding Compounds X:

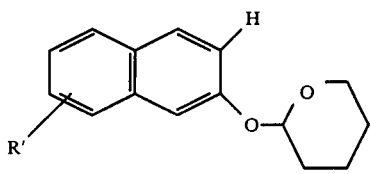
(X)

in which R' is as defined above, by treatment with a lithiating reagent of formula XI:

$$Li-alk \qquad (XI)$$

in which alk is an alkyl radical having from 1 to 6 carbon atoms, branched or unbranched, preferably n-butyl.

Compounds X, in turn, are obtainable by ether-ifing a 2-naphthol of the formula XII:

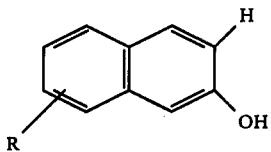
XII in which R' is as defined above, with dihydropyran.

The etherification reaction for preparing Compounds X may be conveniently accomplished by reacting (Step 1) dihydropyran with a compound XII in the presence of strong hydrochloric acid (e.g., 6N concentration), at a reduced temperature, e.g., from about −5° to +15° C., preferably at about +5 to +10° C.; the dihydropyran being present in large excess to serve as solvent. After allowing sufficient time for reaction mixture is neutralized (e.g., by the addition of sodium carbonate) and the resulting compound X recovered by conventional means, e.g., crystallization or extraction.

The lithiated intermediate (VIII) is conveniently prepared by reacting (Step 2) an alkyl lithium reagent (XI) as defined above, in an inert organic solvent, e.g., an ether such as tetrahydrofuran, under essentially anhydrous conditions, at a temperature of from about −5° to +10° C., preferably at from about 0° to +5° C. The alkyl lithium reagent (XI) is conveniently handled in an inert hydrocarbon solvent, e.g., hexane, and added to the reaction mixture in such solution form.

The reaction mixture containing a lithiated compound (VIII) is conveniently used as such (hence, without recovery or separation of VIII) for the "acylation" with a compound IX.

The "acylation" of a lithiated compound (VIII) with a reagent of formula IX, results in the formation of an intermediate which is then hydrolyzed to the desired compound II". The overall "acylation" actually then involves two separate steps (Steps 3 and 4) which are discussed further below.

The reaction of compounds VIII and IX (Step 3) is carried out under essentially anhydrous conditions at reduced temperatures, e.g., from about −50° to −10° C., preferably at from about −40° to −15° C., and in a suitable inert organic solvent, e.g., an aprotic ether, such as tetrahydrofuran.

As noted above, the -Q portion of Compounds IX may be a nitrile or a carboxylate. Hence, the class of compounds IX consists of two sub-classes, namely:

1) 
$$(IX') \quad R^1-C{\equiv}N \text{, and}$$

2)
$$(IX'') \quad R^1-\overset{O}{\underset{\|}{C}}-OR^5$$

in which $R^1$ is as defined above, and $R^5$ is lower alkyl, e.g., having from 1 to 4 carbon atoms, preferably unbranched, such as methyl or ethyl.

While the hydrolysis of intermediate products obtained from the above-described Step 3 of Process d) requires water, the nature of the compound IX used dictates the particular mode of hydrolysis. Hydrolysis is accomplished, when a compound IX' is used, by aqueous mineral acid, preferably strong hydrochloric acid (e.g., 6N) in a water miscible co-solvent, e.g., a lower alkanol such as methanol. However, when a compound IX" is used, the hydrolysis step can be carried out under neutral as well as acidic conditions. Hence, an aqueous salt solution such as brine can alternatively be employed as the hydrolyzing medium. In any event, use of a basic aqueous solution is avoided, so as to avoid difficulties in separation of the reaction mixture which can occur if lithium hydroxide is permitted to form.

The above-described process d) for preparing compounds II" may be conveniently represented by Reaction Scheme D, below, in which R;,$R^1$, alk and Q are as defined above.

REACTION SCHEME D

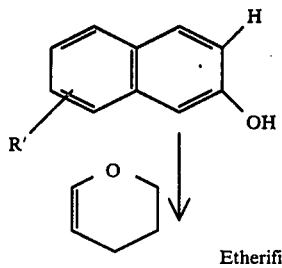
(XII)

Etherification
(Step 1)

(X)

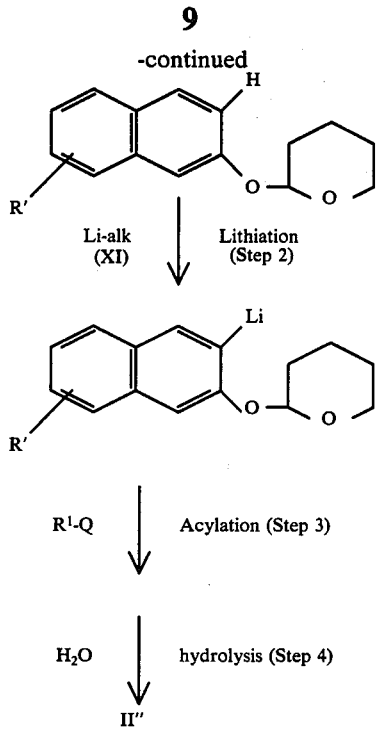

The above-described intermediate compounds II and their preparation do not form part of this invention; methods for the preparation of analogs being described in the literature, e.g., W. J. Houlihan, Journal of Heterocyclic Chemistry 10, 405 (1973). Reagents and reactants described herein, e.g., compounds III, III', IV, V, VI, VII, VIII, IX', IX'', X, XI and XII, are known and obtainable by known means, or where not known, may be obtained by adaptation of methods reported in the literature for the preparation of known analogs; many such compounds being commercially available.

The final products and intermediate compounds described herein may be recovered and refined, where such is desired, by conventional means, such as by crystallization, distillation or chromatographic techniques such as column or thin layer chromatography.

In those above-described reactions calling for anhydrous conditions, such may be achieved by means conventially practiced where it is desired to essentially exclude moisture, e.g., by the use of absolute (dry) reaction medium and reagents, employing moisture-free apparatus and excluding moisture-laden air, e.g., by carrying out reactions in an atmosphere of inert gas and as nitrogen, or by use of moisture traps.

STATEMENT OF UTILITY

The compounds of formula I are useful because they possess pharmacological properties in animals. In particular, such compounds exhibit luteolytic activity and are therefore useful in the control of fertility in female mammals including domestic animals and primates, as they are effective as luteolytic agents which interfere with the course of pregnancy in such mammals. Luteolytic activity is indicated by a rabbit pseudo-pregnancy and a rabbit pregnancy test.

For the luteolytic-pseudopregnancy test, adult New Zealand white female rabbits are injected intraveneously with 100 I.U. of HCG to induce luteal formation (pseudo-pregnancy). Day-1 of pseudopregnancy is the day on which HCG* is injected. On day-3 of pseudopregnancy, females are treated subcutaneously with corn oil (vehicle) or test compound in corn oil, and the treatments are continued through day-8 of pseudopregnancy. Blood samples are collected daily from day-1 through day-12 or on days-1, −5, −9 and −12 of pseudopregnancy and analyzed for plasma progestin content according to the procedure of Johansson et al. (Endocrinology, Vol. 82, pages 143–148, 1968) or plasma progesterone content according to the method of Throneycroft and Stone (Contraception, Vol. 5, pages 129–146, 1972). A compound's relative activity as a luteolytic agent is rated in relation to the degree that the plasma progestin or plasma progesterone levels have returned to pretreatment levels (day-1 values) by day-12 of pseudopregnancy, which are generally less than one nanogram ($10^{-6}$ milligram) per millimeter.

*Human Chorionic Gonadotropin

For the luteolytic pregnant female test, adult, New Zealand white female rabbits are mated to males of known fertility. Double matings are obtained to insure pregnancy. Day-1 of pregnancy is the day on which mating occurs. Treatment (subcutaneous) with either the vehicle (corn oil) as control or vehicle plus compound is initiated during the period that pregnancy depends on corpora luteal activity. For example, in one test embodiment the treatment with the compound is commenced on day-12 of pregnancy and continued through day-16 of pregnancy. Two ml. aliquotes of blood are obtained on days-12, -15, -18 and -21 of pregnancy to determine circulating levels of plasma progesterone to indicate which females are pregnant. In any event, females found not to be pregnant are excluded from the study, and all females are sacrificed on day-21 of pregnancy and the numbers of live and/or dead fetuses recorded.

For the above-described usage, compounds of formula I may be combined with one or more pharmaceutically acceptable liquid carriers, e.g., solvents, diluents and the like, and may be administered parenterally in the form of sterile injectable solutions or suspensions. The pharmaceutical preparations may contain, for example, from about 0.5% up to about 90% of the active ingredient based on the total weight of mixture, i.e., in combination with the carrier, and adjuvants included as desired, more usually between 5% and 70% by weight of such mixture.

Furthermore, the compounds of formula I may be similarly administered in the form of their non-toxic pharmaceutically acceptable acid addition salts. Such salts possess the same order of activity as the free base, are readily prepared by reacting a free base with an appropriate acid and, accordingly, are included within the scope of the invention. Representative of such salts are the mineral acid salts, such as the hydrochloride, hydrobromide, sulfate, phosphate and the like and the organic acid salts such as the benzoate, acetate, maleate, fumarate, p-toluenesulfonate, benzenesulfonate, methanesulfonate and the like.

In general, satisfactory results are obtained when a compound of formula I is administered during the period when maintainence of pregnancy in the host is dependent upon corpora luteal activity, by parenteral administration. Effective dosages will vary depending upon such factors as the particular compound employed and the mode of administration, e.g., whether treatments are given over a series of days or on a single day. However, satisfactory results are generally obtained in female mammals when the compounds are administered at a daily dosage of from about one milligram to about 100 milligrams per kilogram of animal body weight either on a single day or over a series of two or more days. When treatment is to be effected in a single day a dose of from 5 to 100 milligrams per kilograms is considered satisfactory since higher doses are indicated for single day treatment than for multiday treatment. Administration daily may be in a single daily dose or in multiple divided doses to obtain the desired level of administration. For most large mammals, the total daily dosage is from about 5 milligrams to about 500 milligrams for multi-day treatment and from 25 to 2500 milligrams for single day treatment. Dosage forms suitable for parenteral administration comprise from about 5 to about 750 milligrams of the active compound in intimate admixture with a liquid pharmaceutically acceptable carrier. Liquid carriers include sterile water, polyethylene glycols and edible oils such as corn, peanut and sesame oils. Adjuvants, such as a suspending agent, e.g., comprising up to about 5% of the mixture, may be included as desired.

Representative of the evaluation of a compound of this invention in the rabbit pregnancy test (described above) is given in Table I, below, wherein the test compound is 3-(p-chlorophenyl)-1H-benz[f]indazole (final product of Example 1); administered to female rabbits subcutaneously over a series of days (days -12 to -16) or on a single day (either day -5 or -14); females which died during the test, or were found not to be pregnant are not included in the "number of females treated":

TABLE I

| Administration Dose (Mg/ ♀ /day) | Day(s) | No. of females resorbed | No. of females treated |
|---|---|---|---|
| 1 | 12-16 | | 1/4 |
| 2.5 | 12-16 | | 1/3 |
| 5 | 12-16 | | 6/7 |
| 10 | 12-16 | | 3/3 |
| 25 | 5 | | 0/2 |
| 100 | 5 | | 3/4 |
| 250 | 5 | | 4/4 |
| 1 | 14 | | 2/4 |
| 10 | 14 | | 5/8 |
| 25 | 14 | | 6/7 |
| 100 | 14 | | 5/5 |
| 250 | 14 | | 4/4 |

In the following examples which illustrate the invention, temperatures are in degrees centigrade, and room temperature is 20° to 30°.

Particularly preferred compounds are the products of Examples 2 and 10) and 6-bromo-(p-chlorophenyl)-1-methylbenz[f]indazole of Example 8; and especially the product of Example 1.

EXAMPLE 1

3-(p-Chlorophenyl)-1H-Benz[f]indazole

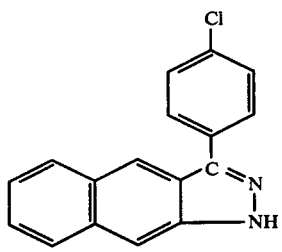

Step 1: 2-hydroxy-3-naphthoyl chloride

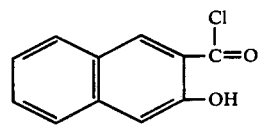

A suspension of 22 g. of 2-hydroxy-3-naphthoic acid in 60 ml of thionyl chloride is refluxed for 1 hour, by which time a clear solution is obtained. The solution is then evaporated under reduced pressure to remove excess thionyl chloride and then benzene is added to the residue and the volatiles are removed again under reduced pressure. Thus is obtained the crude title acid chloride suitable for the next step (2).

Step 2: 3-(p-chlorobenzoyl)-2-naphthol

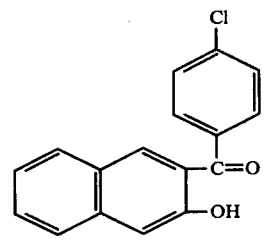

To a solution of 26 g. of crude chloride of Step 1, above, in 500 ml. of chlorobenzene is added portionwise over 15 minutes, 26 g. of anhydrous aluminum chloride. The reaction mixture is then refluxed for 4 hours, cooled and poured into 400 ml. of cold 2N hydrochloric acid solution. The organic layer is separated and the aqueous layer extracted twice with 50 ml. of benzene. The combined benzene solutions are dried (over anhydrous sodium sulfate) and concentrated to a dark oil, which is redissolved in a minimum of benzene and applied to a column of silica-gel. Chromatography using benzene as eluant yields a material which is crystallized from methanol to obtain 3-(p-chlorobenzoyl)-2-naphthol, m.p. 135°-137°.

Step 3: 3-(p-chlorophenyl)-1H-benz[f]indazoale

A solution of 37 g. of the 3-(p-chlorobenzoyl)-2-naphthol of Step 2, above, in a mixture of 300 ml. of diethylene glycol and 75 ml. of hydrazine hydrate is refluxed for 4 hours. It is then cooled and poured on ice-water to yield a precipitate which is collected by filtration. This solid is crystallized from a mixture of methylene chloride (dichloromethane) and ether (1:3) to yield the title product, m.p. 192°.

EXAMPLE 2

3-(p-chlorophenyl)-1-methyl-benz[f]indazole

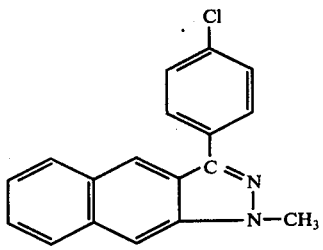

To a solution of 14 g of 3-(p-chlorophenyl)-1H-benz[f]indazole dissolved in 150 ml. dry dimethylacetamide under nitrogen is added 3 g. of a 57% suspension of sodium hydride in mineral oil. The reaction mixture is stirred at room temperature for 1 hour and then 5 ml. of methyl iodide is added. Stirring is continued for 2 hours then the mixture is poured on ice-water, and the precipitate recovered by filtration. The precipitate is recrystallized from ether to yeild the title compound, m.p. 157°–159°.

EXAMPLE 3

3-(p-chlorobenzoyl)-2-naphthol (alternative method).

Step 1: 2-tetrahydropyran-2-yloxy-naphthalene

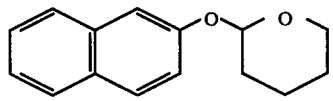

To a solution of 2 drops of 6N hydrochloric acid in 17 g. of dihydropyran is added 14.4 g. of β-naphthol under ice cooling. The resulting solution is stirred at 5° to 10° for 2 hours and then 5 g. of anhydrous sodium carbonate is added. After stirring at room temperature for 15 minutes, the resulting solids are filtered off and the filtrate is concentrated under reduced pressure to yield crude 2-tetrahydropyranyloxynaphthalene, suitable for use in the next step (2).

Step 2: 3-(p-chlorobenzoyl)-2-naphthol

To a solution of 23 g. of the crude tetrahydropyranoyl derivative of Step 1, in 100 ml. of tetrahydrofuran at 0° to 5° under nitrogen, is added 80 ml. of a 1.6M solution of n-butyl lithium in hexane over a period of 20 minutes. After stirring at 0°–5° for 30 minutes the reaction mixture is cooled to −20° and a solution of 14 g. of 4-chlorobenzonitrile in 50 ml. of THF is added over 1½ hours. After stirring at −20° for 2 hours, the mixture is allowed to warm to 0° and maintained there while 200 ml. of sodium chloride solution is added. The organic phase is separated, dried, and concentrated to give a crude intermediate which is dissolved in 500 ml. of methanol containing 100 ml. of 6N hydrochloric acid. The solution is refluxed for 6 hours during which time a precipitate (a side product) forms. The mixture is cooled and the precipitate filtered off. The filtrate is concentrated and the residue crystallized from methanol to give 3-(p-chlorobenzoyl)-2-naphthol which may then be used as described in Step 3 of Example 1, above, to obtain the corresponding indazole product.

EXAMPLE 4

3-(p-chlorobenzoyl)-2-naphthol (additional alternative method)

14.4 g. of β-naphthol is reacted with dihydropyran as described in Step 1 of Example 3, above, and the crude tetrahydropyranyl derivative is also treated with 80 ml. of n-butyl lithium solution as described in Step 2 of Example 3. To this mixture at −35°, under nitrogen, is added a solution of 21.8 g. of methyl p-chlorobenzoate in 100 ml. of tetrahydrofuran. After stirring at −35° for four hours the reaction is worked up as described in Example 3, and then treated with methanol and hydrochloric acid also as described. The crude residue obtained on work-up contains two products which are separated by chromatography on silica-gel and elution with chloroform. The less polar of the two (i.e., eluted first) is isolated and is 3-(p-chlorobenzoyl)-2-naphthol; the more polar product can also be isolated from the later factions and is the undesired isomer, 1-(p-chlorobenzoyl)-2-naphthol, m.p. 162°–165°.

EXAMPLE 5

Following the procedure of Example 1, but using in place of the chlorobenzene used in Step 1, thereof, using an approximately equivalent amount of:
a. benzene;
b. fluorobenzene;
c. bromobenzene;
d. toluene; or
e. methoxybenzene;
there is accordingly obtained:
a. 3-phenyl-1H-benz[f]indazole, m.p. 185°–187°.
b. 3-(p-fluorophenyl)-1H-benz[f]indazole, m.p. 166°–170°.
c. 3-(p-bromophenyl)-1H-benz[f]indazole, m.p. 182°–184°.
d. 3-(p-tolyl)-1H-benz[f]indazole, m.p. 180°–182°; and
e. 3-(p-methoxyphenyl)-1H-benz[f]indazole, m.p. 178°–180°.

EXAMPLE 6

Following the procedure of Example 2, but using in place of the methyliodide used therein, an approximately equivalent amount of:
a. 3-bromo-1-propyne;
b. 3-bromo-1-propene;
c. ethyliodide;
d. 2-propylbromide; or
e. n-propylbromide;
there is accordingly obtained respectively;
a. 3-(p-chlorophenyl)-1-(2-propynyl)-benz[f]indazole, m.p. 138°–140°;
b. 3-(p-chlorophenyl)-1-(2-propenyl)-benz[f]indazole, m.p. 100°–102°;
c. 3-(p-chlorophenyl)-1-ethylbenz[f]indazole, m.p. 116°–118°;
d. 3-(p-chlorophenyl)-1-isiopropylbenz[f]indazole, m.p. 86°–88°; and
e. 3-(p-chlorophenyl)-1-(n-propyl)-benz[f]indazole, m.p. 86°–88°.

EXAMPLE 7

Following the procedures of Examples 4, and Step 3 of Example 1, but using in place of the methyl p-chlorobenzoate used in Example 4, an approximately equivalent amount of methyl isonicotinate, there is accordingly obtained:
a. 3-(4-pyridyl)-1H-benz[f]indazole, m.p. 265°–270°; which upon treatment by the method of Example 2, but using in place of the methyliodide used therein, (adjusting for differences in equivalent weights), 2-propylbromide, there is accordingly obtained:
b. 3-(4-pyridyl)-1 -isopropylbenz[f]indazole, m.p. 135°.

EXAMPLE 8

Following the procedure of Example 1, but using in place of the 2-hydroxy-3-naphthoic acid used therein, an approximately equivalent amount of 6-bromo-2-hydroxy-3-naphthoic acid, there is accordingly obtained 6-bromo-3-(p-chlorophenyl)-1H-benz[f]indazole, m.p. 252°–254°, which upon treatment according to the procedure of Example 2, using methyliodide or 2-propylbromide; (adjusting for differences in equivalent weights of the reactants involved), there is obtained respectively:

6-bromo-3-(p-chlorophenyl)-1-methylbenz[f] indozole, m.p. 178°-180°; and 6-bromo-3(p-chlorophenyl)-1-isopropylbenz [f]indazole, m.p. 252°-254°.

EXAMPLE 9

Following the procedures of Examples 3; Step 3 of Example 1, and Example 2, but using in place of the 4-chlorobenzonitrile used in Example 3, tertiary-butylnitrile (adjusting for differences in equivalent weights), there is accordingly obtained.

a. 3-(tertiary-butyl)-1H-benz[f]indazole, m.p. 117°-118°; and b. 3-(tertiary-butyl)-1-methlbenz[f]indazole, m.p. 116°-118°.

EXAMPLE 10

Following the procedure of Example 8, but starting with benzene instead of the chlorobenzene used therein (and adjusting for differences in equivalent weights), there is accordingly obtained:

a. 6-bromo-3-phenyl-1H-benz[f]indazole, m.p. 206°-208°.

b. 6-bromo-3-phenyl-1-methylbenz[f]indazole, m.p. 172 -174°; and c. 6-bromo-3-phenyl-1-isopropylbenz[f]indazole, m.p. 126°-128°.

EXAMPLE 11

3-(m-methoxyphenyl)-1H-benz[f]indazole

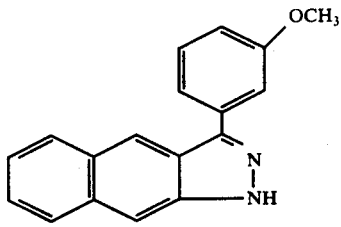

STEP 1: 3-(m-methoxybenzoyl-2-naphthol

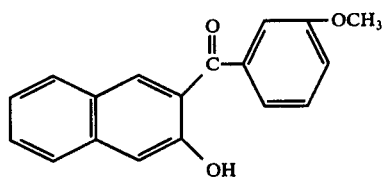

Following the procedure of Example 4, but using in place of the methyl p-chlorobenzoate used therein, an approximately equivalent amount of methyl m-methoxybenzoate, there is accordingly obtained 3-(m-methoxybenzoyl)-2-naphthol.

STEP 2: 3-(m-methoxyphenyl)-1H-benz[f]indazole

Following the procedure of Step 3 of Example 1, but using in place of the 3-(p-chlorobenzoyl-2-naphthol used therein, an approximately equivalent amount of 3-(m-methoxybenzoyl)-2-naphthol, there is accordingly obtained the title product, m.p. 136°-137°.

EXAMPLE 12

Following the procedure of Example 2 but using in place of the 3-(p-chlorophenyl)-1H-benz[f]indazole thereof an approximately equivalent amount of:

a. 3-phenyl-1H-benz[f]indazole (obtainable by Example 5a, above);

b. 3-(-p-bromophenyl)-1H-benz[f]indazole (obtainable by Example 5c, above);

c. 3-(p-methoxyphenyl)-1H-benz[f]indazole (obtainable by Example 5e, above); or d. 3-(m-methoxyphenyl)-1H-benz[f]indazole (obtainable by Example 11, above); there is accordingly obtained:

a. 3-phenyl-1-methylbenz[f]indazole, m.p. 141°-143°;

b. 3-(p-bromophenyl)-1-methylbenz[f]indazole, m.p. 163°-165°;

c. 3-(p-methoxyphenyl)-1-methylbenz[f]indazole, m.p. 103°-105°; and d. 3-(m-methoxyphenyl)-1-methylbenz[f]indazole, m.p. 145°-146°.

EXAMPLE 13

Following the procedure of Example 2 (process b) using as a Compound Ia, 3-(p-methoxyphenyl)-1H-benz[f]indazole (obtainable by Example 5e, above) and as a Compound IV, a) ethyliodide or b) 2-propylbromide, (adjusting for differences in equivalent weights), there is accordingly obtained respectively:

a. 3-(p-methoxyphenyl)-1-ethylbenz[f]indazole, m.p. 112°-114°; and b. 3-(p-methoxyphenyl)-1-isopropylbenz[f]indazole, m.p. 95°-97°.

EXAMPLE 14

Following the procedure of Example 4 and Step 3 of Example 1, but using in place of the methyl p-chlorobenzoate used therein, an approximately equivalent amount of:

a. methyl 3,4-dichlorobenzoate;

b. methyl 3,5-dimethyl benzoate; or c. methyl o-toluate; there is accordingly obtained respectively:

a. 3-(3,4-dichlorophenyl)-1H-benz[f]indazole;

b. 3-(3,5-dimethylphenyl)-1H-benz[f]indazole; and c. 3-(o-tolyl)-1H-benz[f]indazole.

EXAMPLE 15

Following the procedure of Example 1, but using in place of the chlorobenzene used therein, an approximately equivalent amount of:

a. m-xylene;

b. o-methoxytoluene; or c. 1,2-dimethoxybenzene;

there is accordingly obtained respectively:

a. 3-(2,4-dimethylphenyl-1H-benz[f]indazole;

b. 3-(3-methoxy-4-tolyl)-1H-benz[f]indazole; and c. 3-(3,4-dimethoxyphenyl)-1H-benz[f]indazole.

EXAMPLE 16

The following sterile injectable pharmaceutical compositions are formulated with the indicated amounts of active agent using conventional techniques. These injectable compositions represent formulations useful in controlling fertility in the manner described above given daily to a host during the period when maintainence of pregnancy of the host is dependent upon corporaluteal activity.

| Ingredients | Weight (mg) | |
|---|---|---|
| 3-(p-chlorophenyl)-1H-benz[f]indole | 10 | 25 |
| Sodium carboxy methyl cellulose U.S.P. | 1.25 | — |
| Methyl cellulose | 0.4 | — |
| Polyvinylpyrrolidone | 5 | — |
| Lecithin | 3 | — |
| Benzyl alcohol | 0.01 | — |
| Buffer agent to adjust pH for desired stability | q.s.* | — |
| Water | for injection q.s. to 1 ml. | — |
| Corn oil | — | as desired |

*q.s. = quantity sufficient

What is claimed is:

1. A compound which is a benz[f]indazole of the formula:

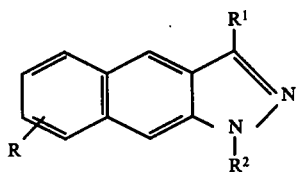

wherein
R is a hydrogen atom, fluoro, chloro, bromo, alkyl having from 1 to 4 carbon atoms or alkoxy having from 1 to 4 carbon atoms;

$R^1$ is substituted or unsubstituted phenyl of the structure:

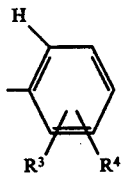

in which $R_3$ and $R_4$ are selected independently from the group consisting of a hydrogen atom, alkyl having from 1 to 4 carbon atoms, alkoxy having from 1 to 4 carbon atoms, fluoro, chloro or bromo; and $R^2$ is a hydrogen atom, alkyl having from 1 to 4 carbon atoms, alkenyl having from 2 to 4 carbon atoms, or alkynyl having from 2 to 4 carbon atoms, provided that:
1. when $R^3$ and $R^4$ are on adjacent carbons, they are not both branched alkyl or alkoxy; and
2. when R is bromo and when $R^3$ is chloro or bromo, then $R^4$ is not chloro or bromo; or a pharmaceutically acceptable acid addition salt thereof.

2. A compound of claim 1 in which $R^2$ is a hydrogen atom.

3. A compound of claim 1 in which $R^2$ is alkyl, alkenyl or alkynyl.

4. A compound of claim 2 in which R is a hydrogen atom.

5. A compound of claim 2 in which R is bromo.

6. A compound of claim 2 in which R is alkyl, alkoxy, fluoro, chloro or bromo.

7. A compound of claim 3 in which R is a hydrogen atom.

8. A compound of claim 3 in which R is bromo.

9. The compound of claim 4 which is 3-(p-chlorophenyl)-1H-benz[f]indazole.

10. The compound of claim 4 which is 3-phenyl-1H-benz[f]indazole.

11. The compound of claim 4 which is 3-(p-fluorophenyl)-1H-benz[f]indazole.

12. The compound of claim 4 which is 3-(p-bromophenyl)-1H-benz[f]indazole.

13. The compound of claim 4 which is 3-(p-tolyl)-1H-benz[f]indazole.

14. The compound of claim 4 which is 3-(p-methoxyphenyl)-1H-benz[f]indazole.

15. The compound of claim 4 which is 3-(m-methoxyphenyl)-1H-benz[f]indazole.

16. The compound of claim 5 which is 6-bromo-3-(p-chlorophenyl)-1H-benz[f]indazole.

17. The compound of claim 5 which is 6-bromo-3-phenyl-1H-benz[f]indazole.

18. The compound of claim 7 which is 3-(p-chlorophenyl)-1-methylbenz[f]indazole.

19. The compound of claim 7 which is 3-(p-chlorophenyl)-1-ethylbenz[f]indazole.

20. The compound of claim 7 which is 3-(p-chlorophenyl)-1-(n-propyl)-benz[f]indazole.

21. The comound of claim 7 which is 3-(p-chlorophenyl)-1-isopropylbenz[f]indazole.

22. The compound of claim 7 which is 3-(p-chlorophenyl)-1-(2-propynyl)benz[f]indazole.

23. The compound of claim 7 which is 3-(p-chlorophenyl)-1-(2-propenyl)benz[f]indazole.

24. The compound of claim 7 which is 3-phenyl-1-methylbenz[f]indazole.

25. The compound of claim 7 which is 3-(p-methoxyphenyl)-1-methylbenz[f]indazole.

26. The compound of claim 7 which is 3-(p-methoxyphenyl)-1-ethylbenz[f]indazole.

27. The compound of claim 7 which is 3-(p-methoxyphenyl)-1-isopropylbenz[f]indazole.

28. The compound of claim 7 which is 3-(m-methoxyphenyl)-1-methylbenz[f]indazole.

29. The compound of claim 7 which is 3-(p-bromophenyl)-1-methylbenz[f]indazole.

30. The compound of claim 8 which is 6-bromo-3(p-chlorophenyl)-1-methylbenz[f]indazole.

31. The compound of claim 8 which is 6-bromo-3-(p-chlorophenyl)-1-isopropylbenz[f]indazole.

32. The compound of claim 8 which is 6-bromo-3-phenyl-1-methylbenz[f]indazole.

33. The compound of claim 8 which is 6-bromo-3-phenyl-1-isopropylbenz[f]indazole.

34. A method of terminating pregnancy in a female mammal which comprises parenterally administering to said mammal during the period when maintainence of pregnancy is dependent upon corpora lateal activity, an amount of a compound of claim 1 effective in terminating pregnancy.

35. The method of claim 34 in which the compound is administered over the course of two or more days in an amount of from about 5 milligrams to about 500 milligrams per day.

36. The method of claim 35 in which the compound is 3-(p-chlorophenyl)-1H-benz[f]indazole.

37. The method of claim 35 in which the compound is 3-(p-chlorophenyl)-1-methylbenz[f]indazole.

38. A pharmaceutical composition suitable for parenteral administration to terminate pregnancy comprising as the active ingredient an effective amount of the compound of claim 1 and a pharmaceutically accceptable liquid carrier therefor.

39. The composition of claim 38 in which the active ingredient is present in an amount of from about 5 milligrams to about 750 milligrams.

40. The composition of claim 39 in which the active ingredient is 3-(p-chlorophenyl)-1H-benz[f]indazole.

41. The method of claim 34 in which pregnancy is terminated by administration in a single day of from 25 to 2500 milligrams of the compound.

* * * * *